(12) United States Patent
Anli et al.

(10) Patent No.: US 7,507,821 B2
(45) Date of Patent: Mar. 24, 2009

(54) PROCESS FOR PREPARING IMATINIB

(75) Inventors: Huang Anli, Shanghai (CN); Liu Xing, Shanghai (CN); Lior Zelikovitch, Mazkeret Batia (IL); Joseph Kaspi, Givatayim (IL)

(73) Assignee: Chemagis Ltd., Bnei-Brak (IL)

( * ) Notice: Subject to any disclaimer, the term of this patent is extended or adjusted under 35 U.S.C. 154(b) by 331 days.

(21) Appl. No.: 11/318,455

(22) Filed: Dec. 28, 2005

(65) Prior Publication Data

US 2006/0149061 A1  Jul. 6, 2006

Related U.S. Application Data

(60) Provisional application No. 60/640,013, filed on Dec. 30, 2004.

(51) Int. Cl.
*C07D 239/00* (2006.01)
*C07D 239/02* (2006.01)

(52) U.S. Cl. .................................................. 544/242
(58) Field of Classification Search ................ None
See application file for complete search history.

(56) References Cited

U.S. PATENT DOCUMENTS 5,521,184 A   5/1996   Zimmermann

FOREIGN PATENT DOCUMENTS

| WO | WO 03/066613 | 8/2003 |
|---|---|---|
| WO | WO 2004/074502 | 2/2004 |

*Primary Examiner*—James O Wilson
*Assistant Examiner*—Noble Jarrell

(57) ABSTRACT

A novel process is disclosed for producing Imatinib, using the precursor 2-chloro-4-(3-pyridyl)-pyrimidine, thus improving Imatinib preparation via an alternative synthetic route, avoiding the use of the toxic reagent cyanamide.

5 Claims, No Drawings

PROCESS FOR PREPARING IMATINIB

RELATED APPLICATIONS

The present application claims priority from U.S. Provisional Patent Application No. 60/640,013, filed on Dec. 30, 2004, which is incorporated herein by reference.

FIELD OF THE INVENTION

The present invention provides a novel process for producing Imatinib avoiding the use of the highly toxic and corrosive reagent cyanamide.

BACKGROUND OF THE INVENTION

Imatinib (N-{5-[4-(4-methyl-piperazinomethyl)-benzoylamido]-2-methylphenyl}-4-(3-pyridyl)-2-pyrimidine-amine) is represented by the following structural formula (I):

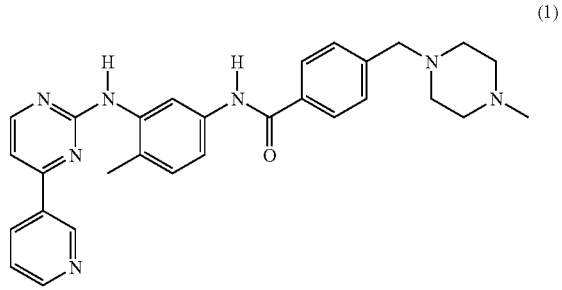

(1)

Imatinib is known as an inhibitor of tyrosine kinases and is indicated for the treatment of chronic myeloid leukemia (CML), Philadelphia chromosome positive leukemia, for patients in chronic phase and in blast crisis, accelerated phase and also for malignant gastrointestinal stromal tumors. It selectively inhibits activation of target proteins involved in cellular proliferation. Imatinib also has potential for the treatment of other cancers that express these kinases, including acute lymphocytic leukemia and certain solid tumors. Imatinib is sold by Novartis as Gleevec™ capsules containing Imatinib mesylate equivalent to 100 mg of imatinib free base.

U.S. Pat. No. 5,521,184 and application WO 03/066613 describe several synthetic routes for preparing Imatinib. One synthetic process, described in Scheme 1, comprises reacting 4-(4-methyl-piperazin-1-ylmethyl)-benzoic acid methyl ester with 3-nitro-4-methyl-aniline to obtain N-(4-methyl-3-nitrophenyl)-4-(4-methyl-piperazin-1-ylmethyl)-benzamide, which is subsequently reduced to obtain N-(3-amino-4-methyl-phenyl)-4-(4-methyl-piperazin-1-ylmethyl)-benzamide. The latter is reacted with cyanamide (NH₂CN) in a mixture of concentrated hydrochloric acid solution and n-butanol to produce N-(3-guanidino-4-methyl-phenyl)-4-(4-methyl-piperazin-1-ylmethyl)-benzamide, which is subsequently reacted with 3-dimethylamino-1-pyridin-3-yl-propenone to obtain Imatinib.

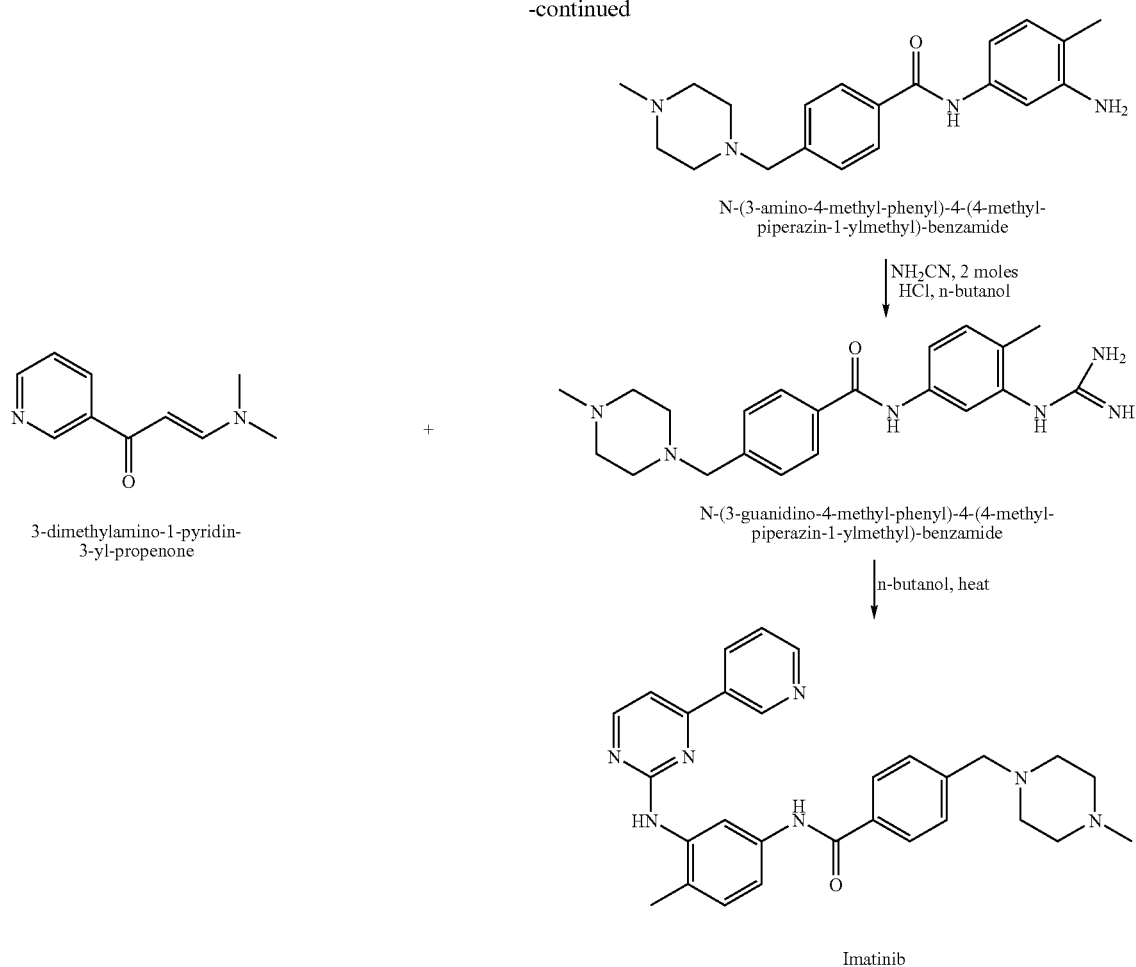

Another process, described in Scheme 2, comprises obtaining 2-methyl-5-nitrophenyl-guanidine from 2-amino-4-nitro-toluene by adding nitric acid to a solution of the latter in ethanol followed by addition of cyanamide. The product is subsequently reacted with 3-dimethylamino-1-pyridin-3-yl-propenone to obtain N-(2-methyl-5-nitrophenyl)-4-(3-pyridyl)-2-pyrimidine-amine, which is subsequently reduced and reacted with 4-(4-methyl-piperazinomethyl)-benzoyl chloride to obtain Imatinib.

Scheme 2

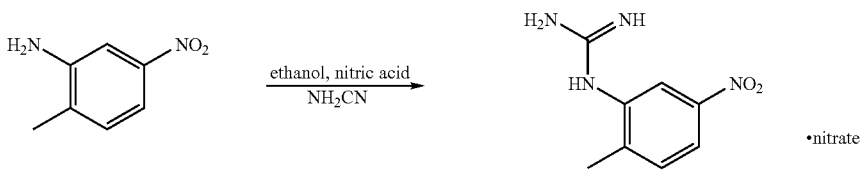

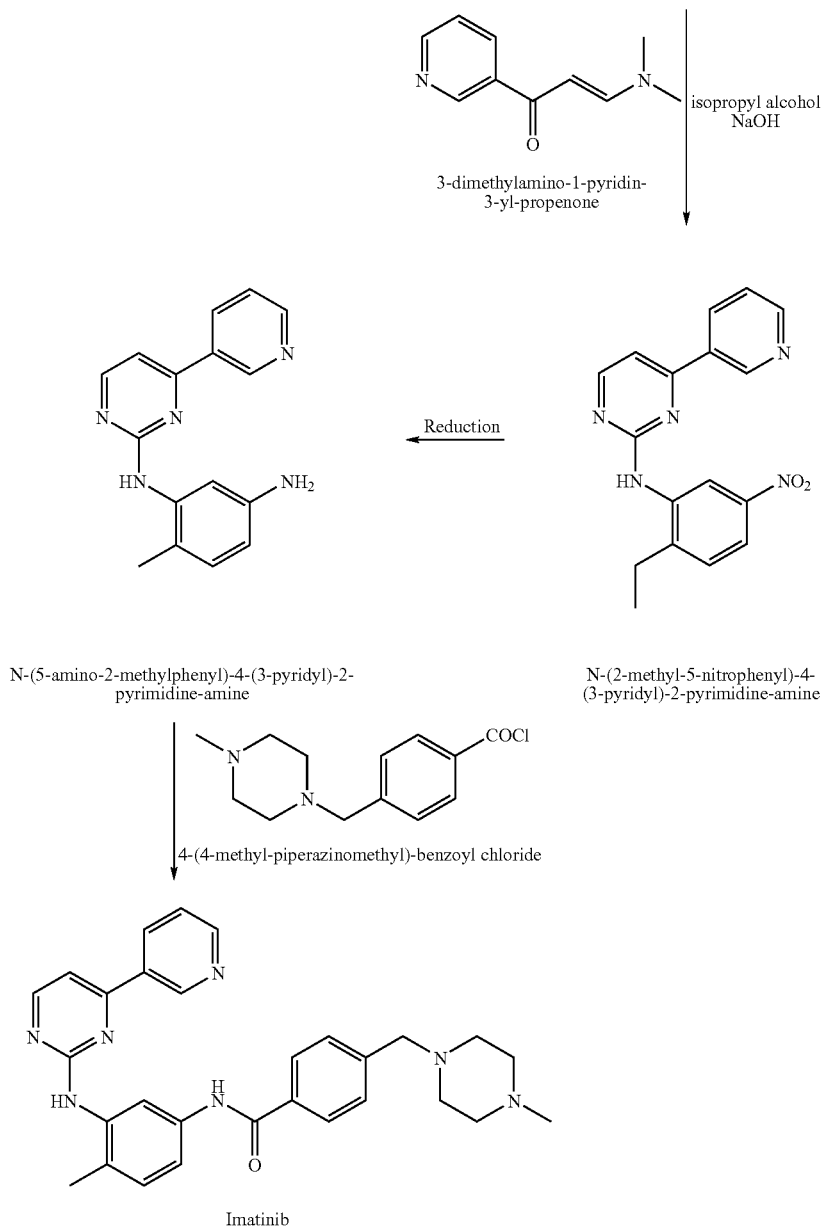

Yet another process, described in Scheme 3, comprises reacting 3-bromo-4-methyl-aniline with 4-(4-methyl-piperazin-1-ylmethyl)-benzoic acid methyl ester to obtain N-(3-bromo-4-methyl-phenyl)-4-(4-methyl-piperazin-1-ylmethyl)-benzamide. The latter is reacted with 4-(3-pyridyl)-2-pyrimidine amine (which is obtained by reacting cyanamide with 3-dimethylamino-1-pyridin-3-yl-propenone) to obtain Imatinib Scheme 3

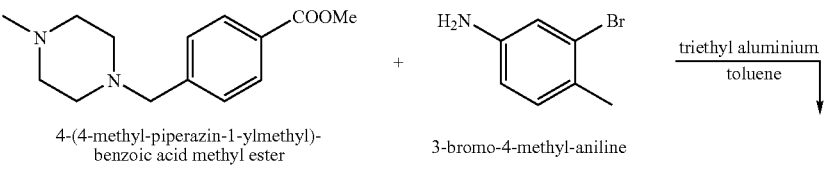

-continued
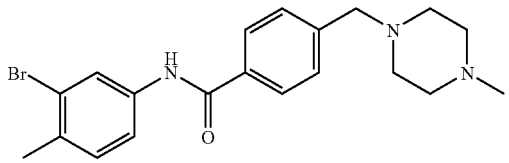
N-(3-bromo-4-methyl-phenyl)-4-(4-methyl-piperazin-1-ylmethyl)-benzamide
3-dimethylamino-1-pyridin-3-yl-propenone
4-(3-pyridyl)-2-pyrimidine-amine
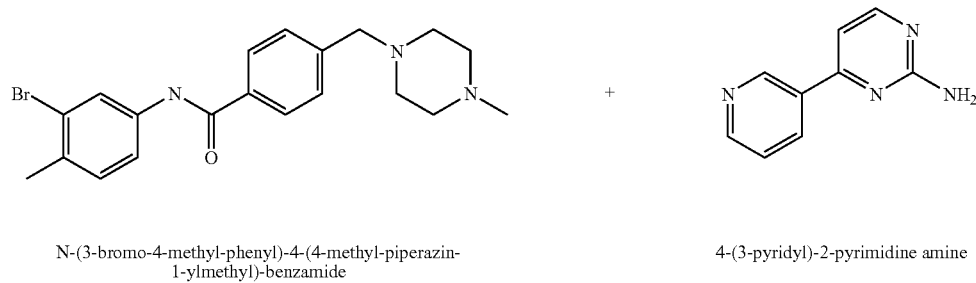
N-(3-bromo-4-methyl-phenyl)-4-(4-methyl-piperazin-1-ylmethyl)-benzamide
4-(3-pyridyl)-2-pyrimidine amine
rac-BINMAP
Pd₂(dba)₃·CHCl₃
sodium tert-butylate
xylene
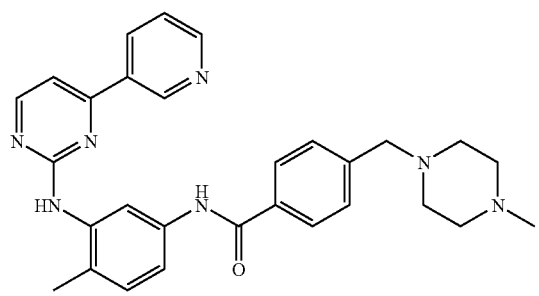
Imatinib The common feature of the above processes for preparing Imatinib, according to U.S. Pat. No. 5,521,184 and application WO 03/066613, which are described herein, is the usage of cyanamide as a reagent. However, the usage of cyanamide in the pharmaceutical industry is disadvantageous, because it is a highly toxic, hazardous and corrosive reagent. Contact of cyanamide with water, acids or alkalies may cause violent reaction and mixing of cyanamide with certain chemicals such as diamines can cause an explosion. The recommended exposure limit of cyanamide is 2 mg per cubic meter and therefore "Good Manufacturing Practice" requires the use of industrial respirators to control the exposure as well as adequate ventilation in the production place. Furthermore, the workers dealing with cyanamide should use appropriate personal protecting clothing to prevent skin contact with cyanamide. These safety measures complicate the production procedures and increase the production costs.

Some other experimental procedures, described in U.S. Pat. No. 5,521,184 and application WO 03/066613, are even less applicable to industrial purposes. These include, for example, the reaction between N-(3-bromo-4-methyl-phenyl)-4-(4-methyl-piperazin-1-ylmethyl)-benzamide and 4-(3-pyridyl)-2-pyrimidine amine which uses a reagent mixture of rac-BINAP (a phosphine oxide catalyst) and $Pd_2(dba)_3$ *$CHCl_3$ (Example 10 in patent application WO 03/066613). These catalysts are very expensive and therefore their use is unfit for commercial production.

The last step in Imatinib synthesis, namely the coupling reaction between N-(5-amino-2-methylphenyl)-4-(3-pyridyl)-2-pyrimidine-amine and 4-(4-methyl-piperazin-1-ylmethyl)-benzoyl chloride is described in application WO 2004/074502, wherein DMF is used instead of pyridine. The inventors of application WO 2004/074502 have stated that using pyridine can be disadvantageous because it is difficult to remove residual traces from the final product.

Therefore, there is a need in the art for a process of preparing Imatinib that is less hazardous and more environmentally friendly.

SUMMARY OF THE INVENTION

The present invention provides an alternative novel synthetic route for preparing Imatinib without using cyanamide.

Thus, Imatinib is obtained by a synthetic route comprising reacting 2-chloro-4-(3-pyridyl)-pyrimidine with 2-amino-4-nitro-toluene to obtain N-(2-methyl-5-nitrophenyl)-4-(3-pyridyl)-2-pyrimidine-amine, which is subsequently reduced and reacted with 4-(4-methyl-piperazine-1-ylmethyl)-benzoyl chloride to yield the final product.

According to one embodiment of the present invention, the starting material 2-oxo-4-(3-pyridyl)-pyrimidine, which is the precursor of 2-chloro-4-(3-pyridyl)-pyrimidine, is prepared from 3-dimethylamino-1-pyridin-3-yl-propenone by a process comprising:

providing a mixture of 3-dimethylamino-1-pyridin-3-yl-propenone, urea and an acid;

heating the mixture to elevated temperature for a time period sufficient to allow completing the reaction;

adding an organic solvent and cooling gradually; and collecting the thus formed precipitate by filtration and washing.

According to yet another embodiment of the present invention, the compound 2-chloro-4-(3-pyridyl)-pyrimidine is prepared by a process comprising:

providing a mixture of 2-oxo-4-(3-pyidyl)-pyrimidine and a chlorinating agent;

heating the mixture to elevated temperature for a time period sufficient to allow completing the reaction;

pouring the reaction mixture into water and adjusting the pH; and extracting with an organic solvent, drying and evaporating the solvent.

According to yet another embodiment of the present invention, the compound N-(2-methyl-5-nitrophenyl)-4-(3-pyridyl)-pyrimidine-amine is prepared by a process comprising:

providing a mixture of 2-chloro-4-(3-pyridyl)-pyrimidine and 2-amino-4-nitrotoluene in an organic solvent;

adding a catalyst, optionally an acid;

heating the mixture to elevated temperature, optionally to reflux, for sufficient time period to allow completing the reaction;

cooling the reaction mixture and adjusting the pH;

evaporating the solvent, washing and extracting the residue; and optionally purifying the reaction product.

According to yet another embodiment of the present invention, N-(5-amino-2-methyl)-4-(3-pyridyl)-pyrimidine-amine is prepared by a process comprising:

providing a suspension of N-(2-methyl-5-nitrophenyl)-4-(3-pyridyl)-pyrimidine-amine in an organic solvent;

adding a catalyst and reacting for a time period sufficient to allow completing the reaction; and filtering out the catalyst and evaporating the solvent.

According to yet another embodiment of the present invention Imatinib base or an acid addition salt thereof is prepared by a process comprising:

providing a mixture of N-(5-amino-2-methylphenyl)-4-(3-pyridyl)-2-pyrimidine-amine and 4-(4-methyl-piperazinomethyl)-benzoyl chloride in an organic solvent;

heating the mixture to elevated temperature for a time period sufficient to allow completing the reaction;

cooling the reaction mixture and adjusting the pH;

evaporating the solvent, washing and extracting the residue; and optionally purifying the reaction product.

DETAILED DESCRIPTION OF THE INVENTION

In a search for a method of preparing Imatinib amenable to industrial use, it has been surprisingly discovered that 2-chloro-4-(3-pyridyl)-pyrimidine can be successfully used as a starting material in an alternative novel synthetic route for preparing Imatinib without using cyanamide.

Thus, Imatinib or an addition salt thereof is obtained by a synthetic route comprising reacting 2-chloro-4-(3-pyridyl)-pyrimidine with 2-amino-4-nitro-toluene to obtain N-(2-methyl-5-nitrophenyl)-4-(3-pyridyl)-2-pyrimidine-amine, which is subsequently reduced and reacted with 4-(4-methyl-piperazine-1-ylmethyl)-benzoyl chloride to yield the final product The process for preparing Imatinib or an addition salt thereof, according to the present invention, is depicted in Scheme 4.

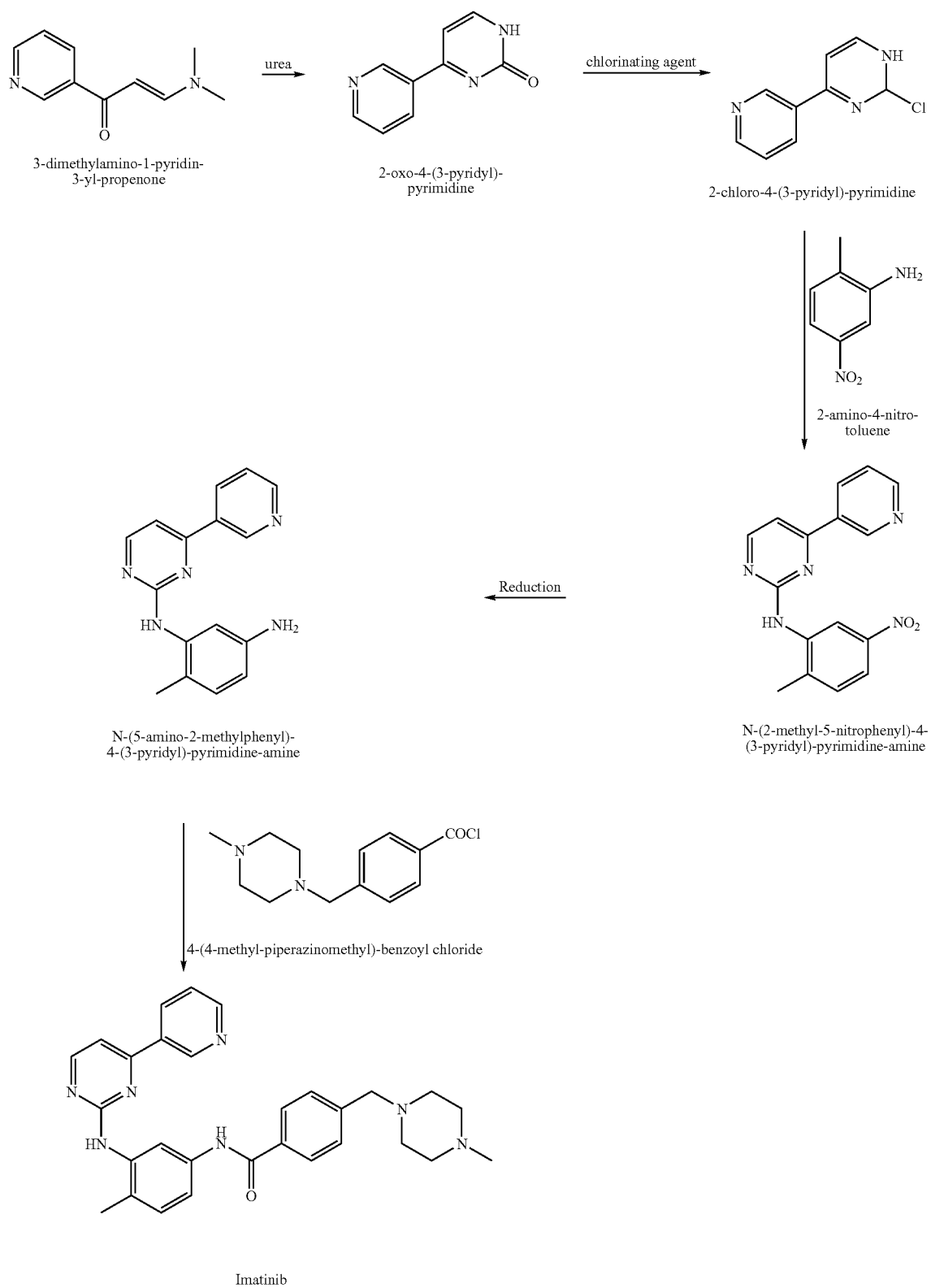

The novel synthetic route depicted in Scheme 4 overcomes the limitations of the process which is described in patent U.S. Pat. No. 5,521,184 and which is depicted in Scheme 2.

The preparation of 4-(4-methylpiperazine-1-ylmethyl)-benzoyl chloride may be carried out according to the prior art methods, and 2-amino-4-nitrotoluene is commercially available.

The starting material 2-chloro-4-(3-pyridyl)-pyrimidine may be preferably obtained by reacting 3-dimethylamino-1-pyridin-3-yl-propenone with urea, to thereby obtain 2-oxo-4-(3-pyridyl)-pyrimidine, which is subsequently reacted with a chlorinating agent such as phosphorus oxychloride.

The usage of urea is highly advantageous, because it is safe, cheap and does not require special means of ventilation during usage.

Another possible synthetic method may be used for preparing 2-chloro-4-(3-pyridyl)-pyrimidine, which is somewhat less advantageous because it should be carried out at low temperature. The process comprises converting 3-bromo-pyridine to 3-pyridinylzinc bromide, which is reacted in situ with 2,4-dichloro-pyrimidine to obtain 2-chloro-4-(3-pyridyl)-pyrimidine. The process is depicted in Scheme 5.

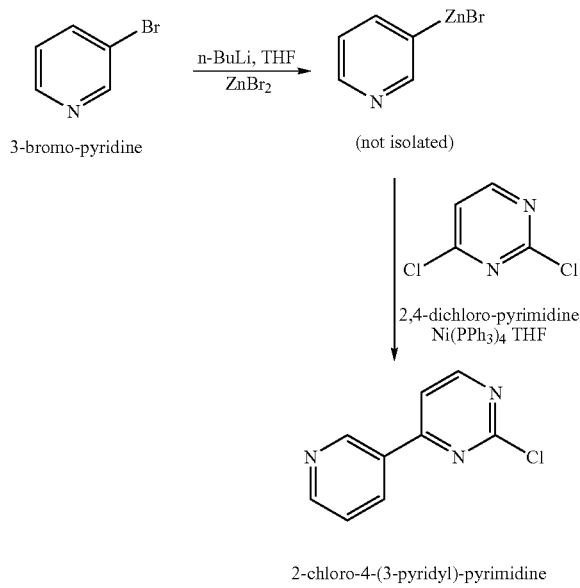

According to one embodiment of the present invention, the starting material 2-oxo-4-(3-pyridyl)-pyrimidine is prepared from 3-dimethylamino-1-pyridin-3-yl-propenone by a process comprising:

providing a mixture of 3-dimethylamino-1-pyridin-3-yl-propenone, urea and an acid;

heating the mixture to elevated temperature for a time period sufficient to allow completing the reaction;

adding an organic solvent and cooling gradually; and collecting the thus formed precipitate by filtration and washing.

According to one aspect of the present invention, the acid used in the process for obtaining the starting material 2-oxo-4-(3-pyridyl)-pyrimidine is selected from the group consisting of hydrochloric acid, hydrobromic acid, sulfuric acid, nitric acid, methanesulfonic acid, and the like. The preferable acid is methanesulfonic acid.

According to another aspect of the present invention the solvent added prior to cooling the reaction mixture is selected from the group consisting of $C_1$-$C_4$ alcohols, e.g., methanol, ethanol, 1-propanol, 2-propanol, 1-butanol, 2-butanol, and mixtures thereof, preferably 1-propanol.

According to another embodiment of the present invention, the compound 2-chloro-4-(3-pyridyl)-pyrimidine is prepared by a process comprising:

providing a mixture of 2-oxo-4-(3-pyidyl)-pyrimidine and a chlorinating agent;

heating the mixture to elevated temperature for a time period sufficient to allow completing the reaction;

pouring the reaction mixture into water and adjusting the pH; and extracting with an organic solvent, drying and evaporating the solvent.

According to yet another aspect of the present invention, the solvent used for extracting is selected from the group consisting of ethyl acetate, dichloromethane, chloroform, toluene, and the like, and mixtures thereof. Preferably, the solvent is ethyl acetate.

According to yet another aspect of the present invention the chlorinating agent is selected from the group consisting of phosphorous oxychloride, phosphorous trichloride, thionyl chloride, oxalyl chloride, phosphorus pentachloride and the like.

Preferably, the chlorinating agent is phosphorous oxychloride.

According to yet another aspect of the present invention, the chlorinating agent is used in the process as a reagent as well as a solvent. While using reflux conditions in the chlorinating process, bumping may occur several hours after starting the reaction, especially in cases when the concentration of the reaction mixture is greater than 1 g/4 ml. Increasing the amount of $POCl_3$ and reacting at lower temperature of about 50° C. can cause elimination of the bumping problem from reoccurring.

According to yet another embodiment of the present invention, the compound N-(2-methyl-5-nitrophenyl)-4-(3-pyridyl)-pyrimidine-amine is prepared by a process comprising:

providing a mixture of 2-chloro-4-(3-pyridyl)-pyrimidine and 2-amino-4-nitrotoluene in an organic solvent;

adding a catalyst, optionally an acid;

heating the mixture to elevated temperature, optionally to reflux, for a time period sufficient to allow completing the reaction;

cooling the reaction mixture and adjusting the pH;

evaporating the solvent, washing and extracting the residue; and optionally purifying the reaction product.

According to yet another aspect of the present invention, the acid used in the process is selected from the group consisting of hydrochloric acid, hydrobromic acid, sulfuric acid, nitric acid, methanesulfonic acid, and the like. The preferable acid is hydrochloric acid.

According to yet another aspect of the present invention, the solvent used in the process is selected from the group consisting of $C_1$-$C_4$ alcohols, e.g., methanol, ethanol, 1-propanol, 2-propanol, 1-butanol, 2-butanol, isobutanol, and mixtures thereof, preferably 1-butanol.

According to yet another aspect of the present invention, the compound N-(2-methyl-5-nitrophenyl)-4-(3-pyridyl)-pyrimidine-amine can be purified by any conventional method known in the art selected, without limitation, from the group consisting of precipitation, crystallization, slurrying, washing in a suitable solvent, column chromatography, dissolution in an appropriate solvent (e.g., dichloromethane) and re-precipitation by addition of a second solvent in which the compound is insoluble, and any combination of methods thereof.

When a slurrying procedure is applied to purify the compound N-(2-methyl-5-nitrophenyl)-4-(3-pyridyl)-pyrimidine-amine, the organic solvent used in this procedure may be selected from the group consisting of water, methanol, ethanol, 1-propanol, 2-propanol, and mixtures thereof. The presently most preferred organic solvents used in the slurrying procedure are methanol and water.

According to yet another embodiment of the present invention N-(5-amino-2-methyl)-4-(3-pyridyl)-pyrimidine-amine is prepared by a hydrogenation process comprising:

providing a suspension of N-(2-methyl-5-nitrophenyl)-4-(3-pyridyl)-pyrimidine-amine in an organic solvent;

adding a catalyst and reacting for a sufficient time period to allow completing the reaction; and filtering out the catalyst and evaporating the solvent.

According to yet another aspect of the present invention, the solvent used for carrying out the hydrogenation process is selected from the group consisting of methanol, ethanol, ethyl acetate, dichloromethane, chloroform, acetic acid and mixtures thereof. Preferably, the solvent is ethyl acetate.

According to yet another aspect of the present invention, the catalyst used in the hydrogenation process is selected from the group consisting of Raney Ni, palladium on activated carbon, palladium on sulfided carbon, platinum on activated carbon, platinum on sulfided carbon and the like, preferably palladium on activated carbon.

According to yet another embodiment of the present invention, Imatinib base or an acid addition salt thereof is prepared by a process comprising:

providing a mixture of N-(5-amino-2-methylphenyl)-4-(3-pyridyl)-2-pyrimidine-amine and 4-(4-methyl-piperazinomethyl)-benzoylchloride in an organic solvent;

heating the mixture to elevated temperature, for a time period sufficient to allow completing the reaction;

cooling the reaction mixture and adjusting the pH;

evaporating the solvent, washing and extracting the residue; and optionally purifying the reaction product.

According to yet another aspect of the present invention, the crude Imatinib base can be purified by any conventional method known in the art selected, without limitation, from the group consisting of precipitation, crystallization, slurrying, washing in a suitable solvent, column chromatography, and any combination of methods thereof.

According to one aspect of the present invention, the purification of the crude Imatinib base can be carried out by slurrying it at least one time in an organic solvent.

According to yet another aspect of the present invention, the solvent used for the slurrying procedure is selected from the group consisting of ethyl acetate, diethyl ether, diisopropyl ether, methyl tert-butyl ether, hexane, cyclohexane, petroleum ether and mixtures thereof. Preferably, the solvent used in the slurrying procedure is ethyl acetate.

EXAMPLES

1. Preparation of 2-oxo-4-(3-pyridyl)-pyrimidine

A 250 ml two necked flask, equipped with a mechanical stirrer and a condenser, was charged with 3-dimethylamino-1-pyridin-3-yl-propenone (10 grams, 0.0567 mole) followed by addition of methanesulfonic acid (1.2 ml, 0.0165 mole). The mixture was heated at 145-150° C. under vigorous stirring for 4.5 hours. Then, the reaction mixture was cooled to 90° C. and 1-propanol (70 ml) was added. The mixture was stirred at 80° C. for 1 hour and then cooled to 15° C. A precipitate was collected by filtration and dissolved in water (150 ml) while heating to 80° C. The mixture was cooled gradually to 20° C. for 2 hours, and a precipitate was collected by filtration, washed with cold water (2×20 ml) and dried at 85° C. overnight to give 37.76 g of 2-oxo-4-(3-pyidyl)-pyrimidine in 60% yield, having a purity of 99.4%.

2. Preparation of 2-chloro-4-(3-pyridyl)-pyrimidine

In a 250 ml two necked flask, equipped with a mechanical stirrer and a condenser, a mixture of 2-oxo-4-(3-pyidyl)-pyrimidine (3 g, 0.017 mol) and $POCl_3$ (18 ml) was stirred at 50° C. for 4.5 hrs. The reaction mixture was poured into cold water (50 ml) and neutralized with 47% aqueous NaOH solution to pH 8. The solution was extracted with ethyl acetate (2×50 ml). The combined ethyl acetate phase was dried over magnesium sulfate and evaporated to dryness to give 2-chloro-4-(3-pyridyl)-pyrimidine in 56% yield, having a purity of 97%.

3. Preparation of N-(2-methyl-5-nitrophenyl)-4-(3-pyridyl)-pyrimidine-amine

A 250 ml reactor, equipped with a mechanical stirrer and a reflux condenser, was charged with 2-chloro-4-(3-pyridyl)-pyrimidine (0.5 g, 2.6 mmol), 2-amino-4-nitrotoluene (0.5 g, 3.2 mmol), n-butanol (15 ml) and concentrated HCl (5 drops) and the mixture was refluxed for 38 hours. Then, the mixture was cooled, and 6 N NaOH was added to pH 8. The solvent was evaporated under reduced pressure and water (20 ml) was added to the residue, followed by extraction with dichloromethane (2×20 ml). The combined organic phase was concentrated to dryness to give the crude N-(2-methyl-5-nitrophenyl)-4-(3-pyridyl)-pyrimidine-amine, which was purified by column chromatography to yield a product having 80% purity. The residue was re-slurried twice in methanol (2×2 ml) and in water (3 ml) and dried under reduced pressure.

4. Preparation of N-(5-amino-2-methyl)-4-(3-pyridyl)-pyrimidine-amine

A 1000 ml reactor, equipped with a mechanical stirrer and a reflux condenser, was charged with N-(2-methyl-5-nitrophenyl)-4-(3-pyridyl)-pyrimidine-amine (36.5 g) and ethyl acetate (550 ml) was added into the reactor to obtain a suspension. 10% palladium on activated carbon (18 g) was then added. The hydrogen reduction was carried on at 25□ and ~4 atm until no hydrogen was absorbed anymore. The reaction mixture was then filtered, and the thus obtained solution was evaporated under reduced pressure to dryness to give 31 g of crude product in an yield of 94%, having a purity of 96%.

5. Preparation of Imatinib Free Base

A mixture of 8.6 g (0.031 mol) N-(5-amino-2-methylphenyl)-4-(3-pyridyl)-2-pyrimidine-amine and 12.6 g (0.038 mol) of 4-(4-methyl-piperazinomethyl)-benzoyl chloride in pyridine (350 ml) were stirred under nitrogen at 50° C. for 4.5 hours. The solvent was evaporated under reduced pressure at a temperature of about 70° C. Water (350 ml) was added, and the solution was basified to pH 10 with 6N NaOH (about 20 ml). The aqueous solution was extracted with dichloromethane (2×250 ml), and dried over $Na_2SO_4$. After the solvent was evaporated, ethyl acetate was added to the thus formed residue (80 ml), which was slurried and filtered.

Another portion of ethyl acetate was added (40 ml) and the residue was slurried for one more time, filtered and dried to give N-{5-[4-(4-methyl-piperazinomethyl)-benzoylamido]-2-methylphenyl}-4-(3-pyridyl)-2-pyrimidine-amine (Imatinib) in 70% yield, having a m.p of 210-213° C., and a purity of 97%, by HPLC.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A process for preparing Imatinib or an addition salt thereof, wherein the compound 2-chloro-4-(3-pyridyl)-pyrimidine, is used as starting material, wherein the compound 2-chloro-4-(3-pyridyl)-pyrimidine is reacted with 2-amino-4-nitrotoluene to obtain N-(2-methyl-5-nitrophenyl)-4-(3-pyridyl)-2-pyrimidine-amine, which is subsequently hydrogenated to obtain N-(5-amino-2-methyl)-4-(3-pyridyl)-pyrimidine-amine, which is reacted with 4-(4-methyl-piperazine-1-ylmethyl)-benzoyl chloride, as depicted in Scheme 4.

2. A process for preparing Imatinib or an addition salt thereof, according to claim 1, the process comprising:
    providing a mixture of N-(5-amino-2-methylphenyl)-4-(3-pyridyl)-2-pyrimidine-amine and 4-(4-methyl-piperazinomethyl)-benzoyl chloride in an organic solvent;
    heating the mixture to elevated temperature for a time period sufficient to allow completing the reaction;
    cooling the reaction mixture and adjusting the pH;
    evaporating the solvent, washing and extracting the residue; and
    optionally purifying the reaction product.

3. The process for preparing Imatinib base or an addition salt thereof, according to claim 2, wherein the crude Imatinib base is purified by using a method selected from the group consisting of precipitation, crystallization, slurrying, washing in a suitable solvent, column chromatography, and any combination of methods thereof.

4. The process for preparing Imatinib or an addition salt thereof, according to claim 3, wherein the crude Imatinib base is purified by slurrying procedure in a solvent selected from the group consisting of ethyl acetate, diethyl ether, diisopropyl ether, methyl tert-butyl ether, hexane, cyclohexane, petroleum ether and mixtures thereof.

5. The process for preparing Imatinib base or an addition salt thereof, according to claim 4, wherein crude Imatinib base is purified by slurrying procedure in ethyl acetate.

* * * * *